United States Patent [19]

Becker et al.

[11] Patent Number: 5,403,942
[45] Date of Patent: Apr. 4, 1995

[54] PROCESS FOR THE PREPARATION OF ALUMINOXANES

[75] Inventors: Ralf-Jurgen Becker, Hamm; Stefan Gurtzgen, Wuppertal; Rolf Schrader, Unna, all of Germany

[73] Assignee: Witco GmbH, Bergkamen, Germany

[21] Appl. No.: 213,948

[22] Filed: Mar. 16, 1994

[30] Foreign Application Priority Data

May 6, 1993 [DE] Germany .................. 43 14 986.3

[51] Int. Cl.$^6$ ............................................. C07F 5/06
[52] U.S. Cl. .............................. 556/175; 556/179; 556/182; 556/187
[58] Field of Search ............... 556/175, 179, 182, 187

[56] References Cited

U.S. PATENT DOCUMENTS

| | | | |
|---|---|---|---|
| 3,242,099 | 3/1966 | Manyik et al. | 252/429 |
| 4,542,199 | 9/1985 | Kaminsky et al. | 526/160 |
| 4,544,762 | 10/1985 | Kaminsky et al. | 556/179 |
| 4,772,736 | 9/1988 | Edwards et al. | 556/179 |
| 4,924,018 | 5/1990 | Bottelberghe | 556/179 |

OTHER PUBLICATIONS

Kaminisky et al. *Makromol. Chem., Macrol. Symp.,* 3, 377–387 (1986).
Kaminsky, *Nachr. Chem. Tech. Lab.,* 29, 373–377 (1981).

*Primary Examiner*—José G. Dees
*Assistant Examiner*—Porfirio Nazario-Gonzalez
*Attorney, Agent, or Firm*—Scully, Scott, Murphy & Presser

[57] ABSTRACT

The invention relates to a process for the preparation of aluminoxanes by addition of water to a solution of trialkylaluminum in an inert solvent, characterized in that the water required for the reaction is metered via a mixing nozzle into a static mixer, in particular a jet loop reactor.

8 Claims, 2 Drawing Sheets

PROCESS FOR THE PREPARATION OF ALUMINOXANES

BACKGROUND OF THE INVENTION

The invention relates to the preparation of aluminoxanes by addition of water to a solution of trialkylaluminum in an inert solvent, the water required for the reaction being metered via a mixing nozzle into a static mixer, in particular a jet loop reactor.

Longer-chain oligomeric and/or polymeric alkylaluminoxanes of the simplified structures

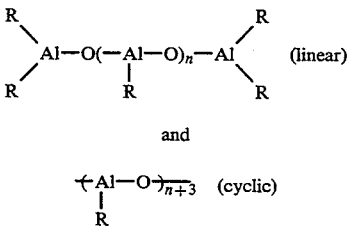

and $$\leftarrow\text{Al}-\text{O}\rightarrow_{n+3} \quad \text{(cyclic)}$$
$$\phantom{xx}|\phantom{xx}$$
$$\phantom{xx}R\phantom{xx}$$

are known compounds, which are used as catalyst components in the preparation of high-activity polyolefin catalysts, for which some sources mention oligomeric methylaluminoxanes (MAO) with R=$CH_3$ as preferred. The degree of oligomerization n here plays an important role in the activity of the polyolefin catalysts, as was established by determination of the dependence of the catalyst activity on the average molecular weight of the aluminoxanes used (lit.: W. Kaminsky, Nachr. Chem. Tech. Lab. 29, 373–7 (1981); W. Kaminsky et al., Makromol. Chem., Macromol. Symp. 3, 377–87 (1986)).

The reaction of trialkylaluminums with water in inert hydrocarbons is mentioned in the literature as the known preparation process for alkylaluminoxanes. However, for the preparation of oligomeric methylaluminoxanes (MAO) from trimethylaluminum (TMA), other methods have also been mentioned as preferred, since it is known from the literature that the preparative method of slowly adding water to trimethylaluminum (TMA), described in more detail in, for example, U.S. Pat. No. 3,242,099, gives MAO only with difficulty and in very poor yield (EP-A-0 108 339); in addition, this method results in products which, in combination with the transition metal component, do not give high-activity catalyst systems (EP-B-0 069 951).

According to U.S. Pat. No. 4,924,018, an emulsion of from 0.5 to 10% of water in toluene is metered into a solution of trimethylaluminum, for example. The concentration of the resulting MAO solution and thus also the space-time yield are very low.

Furthermore, the addition of water to a solution of triisobutylaluminum (TIBA) (U.S. Pat. No. 4,772,736) in the shear field of a stirrer is described for a stirred reactor on a laboratory scale. The application of this process to a large industrial scale would be completely uneconomical, if not impossible, because of the disproportionately increasing stirring energy.

BRIEF SUMMARY OF THE INVENTION

Surprisingly, it has now been found that aluminoxanes, including in particular methylaluminoxane, can be prepared directly in solutions of high concentration and in high yield from the corresponding trialkylaluminums, if the reaction is carried out in a static mixer. The average molecular weight of the aluminoxanes so formed can be controlled to meet the requirements of the olefin polymerization process, principally by adjusting the ratio of water to trialkylaluminum (with a higher water content leading to higher degree of polymerization).

The invention accordingly relates to a process for the preparation of aluminoxane of the general formula $R_2AlO[RAlO]_nAlR_2$ or the general formula $-[-RAlO-]-_{n+3}$ or more frequently both formulas, wherein each R is independently branched or linear alkyl containing 1 to 10 carbon atoms and each n is an integer from 0 to 20, by addition of water to a solution of trialkylaluminum of the formula $AlR_3$ in an aliphatic, cycloaliphatic or aromatic hydrocarbon, whereby said water reacts with said trialkylaluminum to form said aluminoxane, which is characterized in that the water required for the reaction is metered via a mixing nozzle into said solution in a static mixer.

DETAILED DESCRIPTION OF THE DRAWINGS

DETAILED DESCRIPTION OF THE INVENTION

In static mixers, a forced homogenization of the components to be mixed is effected without moving internal elements. In these mixers, unlike dynamic mixers, the material to be mixed is moved past the non-mobile (static) internal elements of the vessel.

These internal elements may have the most diverse variations in geometric form, but function as actual mixing elements to effect an intensive in-line mixing of the feedstock/product streams.

Suitable static mixers for carrying out the process of the invention are, in particular, jet loop reactors (JLR).

The mode of action of the JLR preferably used according to the invention, the BURDOSA reactor, as described for example in U.S. Pat. No. 4,037,825, is based on a liquid propulsion jet in the inside tube which imparts an impulse to the total reactor contents and thus induces a high circulating flow. This results in the circulating flow of liquid in the reactor being about 8 to 10 times higher than the propulsion jet volume flow.

Figure 2:
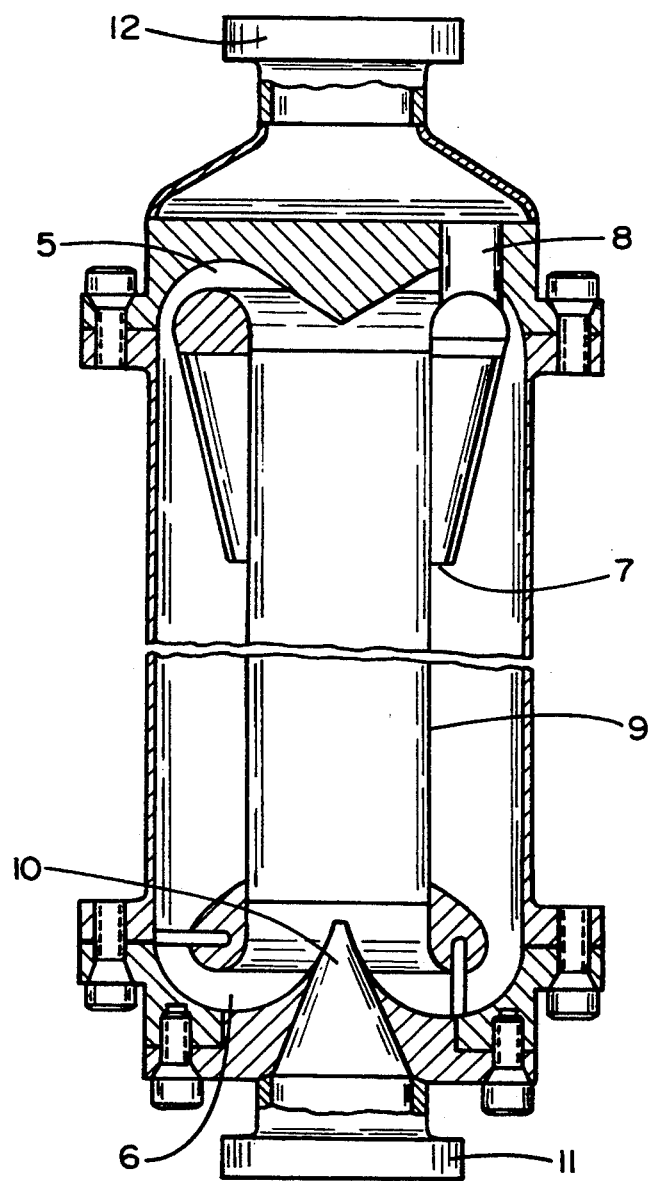
FIG. 2 is a cross-sectional view of a jet loop reactor useful in carrying out the process of the present invention.

The flow in the reactor is in fact approximately as follows, referring to FIG. 2. The material to be mixed entering at the bottom center (11) of the reactor via the injection nozzle (10) is, by means of a bow-shaped configuration (5) at the upper end, made to flow back along the outer wall and, by means of a bow-shaped configuration (6) at the lower end, forced alongside the propulsion jet. On each further circulation, the recirculated liquid is mixed with the in coming liquid a part of the liquid is flowing to the outer wall of the insert tube (9). Through the slot outlet (7) via the product exit opening (8) and the product outlet 12) the liquid is flowing out of the reactor.

In the process of the invention, water is metered in via the mixing nozzle into the jet loop reactor in a volume flow ratio of water:trialkylaluminum solution of from 1:500 to 1:40,000, preferably from 1:2,000 to 1:20,000.

The jet loop reactor, because of the high circulating flow, provides good and extremely rapid mixing of the alkylaluminum-containing solution with water. Due to the high primary dispersal, it is possible to avoid a localized excessive concentration of water, which would otherwise lead to losses in yield and an undesirably high proportion of unreacted trialkylaluminum.

Even at high metering-in rates, localized overheating caused by the strongly exothermic reaction of alkylaluminums with water can be avoided.

The process of the invention is distinguished from the prior art represented by U.S. Pat. No. 4,772,736 by a higher space-time yield, simpler practical preparability of alkylaluminumoxanes and improved material and energy dissipation, and also a significantly higher yield based on aluminum. In addition, the average degree of oligomerization n, which is reflected in the average molecular weight of the reaction product, can be specifically influenced by appropriate metering of the reactants and control of the reaction parameters. The molar ratio $H_2O$:trialkylaluminum, particularly also for trimethylaluminum (TMA), can thus be set to the desired value, with a higher relative amount of water leading to a higher degree of oligomerization. This is of particular significance, since the activity of aluminoxanes as cocatalysts in the olefin polymerization is evidently dependent on the degree of oligomerization of the aluminoxane used (lit.: W. Kaminsky, Nachr. Chem. Tech. Lab. 29, 373–7 (1981); W. Kaminsky et al., Makromol. Chem., Macromol. Symp. 3, 377–87 (1986)).

In the preparation of the aluminoxanes according to the invention, it is possible to use trialkylaluminum compounds of the formula $Al(R)_3$, where R is any alkyl radical having from 1 to 20 carbon atoms, such as ethyl, propyl, butyl, pentyl, octyl, 2-ethylhexyl and isopropyl radicals, being no problem even with trimethylaluminum, which because of its high reactivity is particularly difficult to convert to a defined product in a controlled process.

The molar ratio of $H_2O$:trialkylaluminum can, depending on the chain length of the alkyl radical, be set to the range of 0.6–1.2:1, preferably, to the range of 1:1. For the preferred trimethylaluminum, the ratio is maintained, according to the invention, in the range from 0.65:1 to 0.75:1.

In this range there is obtained a very active methylaluminoxane (MAO) which has a sufficiently high average molecular weight and good solubility in alkylbenzenes, for example toluene. The proportion of insoluble by-products is low and can easily be separated off by the customary methods.

The starting materials are used in amounts such that the concentration of the aluminoxane in the solvent employed is in the range of 1–20% by weight, preferably 1–10% by weight.

Suitable solvents are, in particular, aliphatic, cycloaliphatic or aromatic hydrocarbons such as pentane, hexane, heptane, octane, cyclohexane, methylcyclohexane and, in the case of the preparation of methylaluminoxane, preferably toluene and xylene.

Due to the reactivity of the organoaluminum compounds toward moisture and atmospheric oxygen, the process should be carried out under a dry inert gas atmosphere.

The reaction is generally carried out at temperatures between −20° C. and +100° C., preferably between +10° C. and +30° C.

The reaction product obtained is a solution of an oligomeric alkylaluminoxane, which solution contains unreacted trialkylaluminum in free and/or complexed form.

Figure 1:
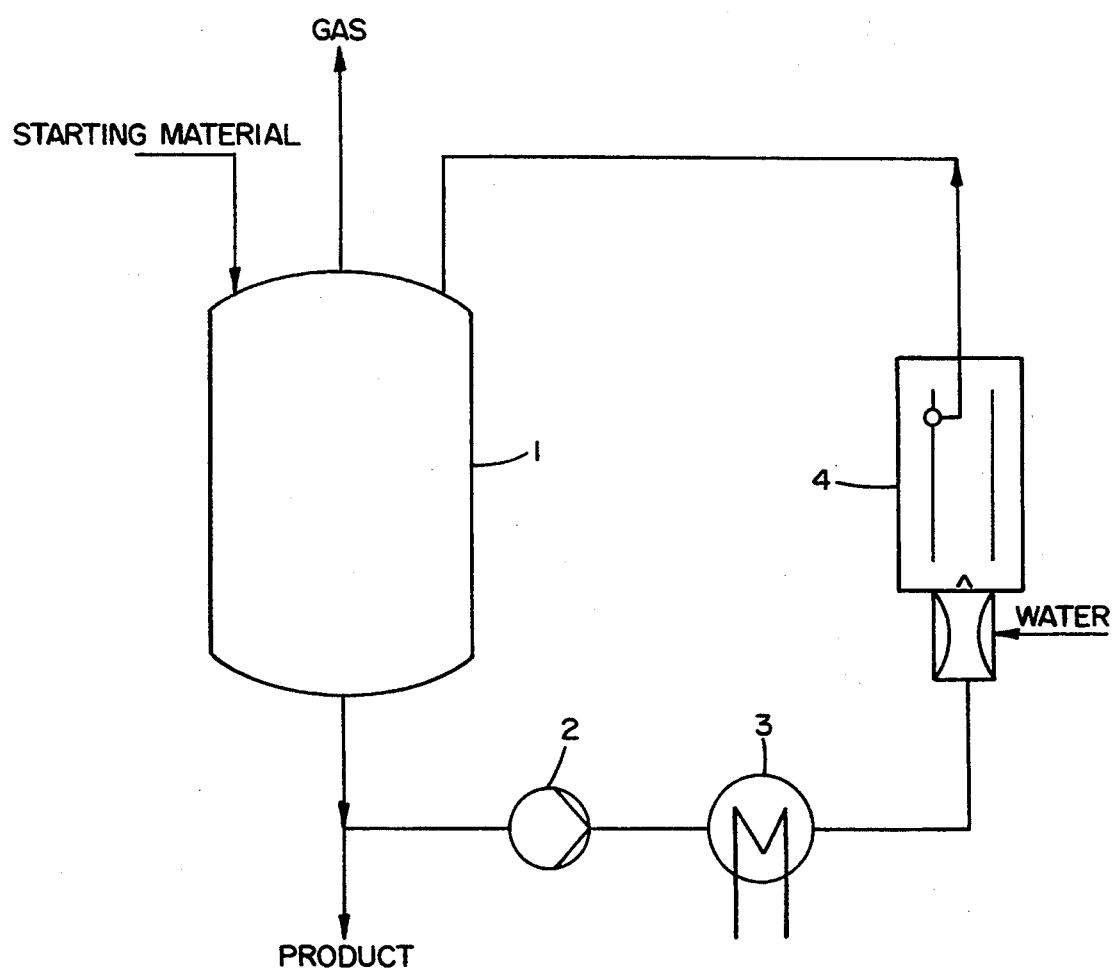
FIG. 1 is a flowchart showing an overall process scheme embodying the process of the present invention.

FIG. 1 shows the plant layout for a process of the present invention using a jet loop reactor (JLR). A stock tank 1 is charged with a solution of an alkylaluminum in a solvent. This solution is conveyed by a pump 2 through a heat exchanger 3 and conveyed in a cooled state into the JLR 4 and is mixed with water in a definite volume flow ratio of, for example, 1:10,000. Localized overheating due to the exothermic reaction is avoided by back-mixing in the JLR. The gas formed in the case of alkyls having short-chain alkyl groups (e.g. methane, butane) is separated from the liquid.

EXAMPLES

Example 1

The stock vessel was charged with 628 kg of a 16% strength trimethylaluminum (TMA) solution in toluene. This solution was circulated by pumping through the jet loop reactor (JLR) (Burdosa reactor), a heat exchanger and a gas separator (FIG. 1). Into this TMA/toluene solution, 17 kg of water (molar ratio of TMA:$H_2O$ = 1:0.68) were metered in at 25° C. into the JLR in a volume flow ratio of 1:6,000. The MAO content of the solution was 10.2%; the yield, based on the aluminum content of the solution, was 92%. The cryoscopic determination of the average molecular weight gave 1000 g/mol. This is calculated to correspond to an average degree of oligomerization of about 15.

A comparison (see table) shows the high yield of dissolved alkylaluminum in contrast to the prior art (U.S. Pat. No. 4,772,736).

TABLE

|  | Charge Al (%) | Product Al (%) | Yield (%), based on Al |
|---|---|---|---|
| Comparative examples according to U.S. Pat. No. 4,772,736 | 7.5 | 5.85 | 78.0 |
|  | 8.1 | 6.5 | 80.2 |
| Example 1 | 6.0 | 5.56 | 92.0 |

Example 2

Example 1 was followed by the stock vessel was charged with 495 kg of n-heptane, 82.5 kg of TMA and 32.5 kg of TIBA. 15.0 kg of water were metered into this circulating material via the JLR in a volume flow ratio of 1:2,000. 497 kg of a 10.5% strength aluminoxane solution were obtained in a yield comparable to that of Example 1. The average molecular weight was determined cryoscopically as 950 g/mol.

Example 3

The stock vessel was charged with 628 kg of a 16% strength trimethylaluminum (TMA) solution in toluene. This solution was circulated by pumping through the jet loop reactor (JLR) (Burdosa reactor), a heat exchanger and a gas separator (FIG. 1). Into this TMA/toluene solution, 17 kg of water (molar ratio of TMA:$H_2O$ = 1:0.68) were metered at 25° C. into the JLR in a volume flow ratio of 1:20,000. The MAO content of the solution was 10.4%; the yield, based on the aluminum content of the solution, was 93.5%. The cryoscopic determination of the average molecular weight gave 1000 g/mol. This is calculated to correspond to an average degree of oligomerization of about 15.

Example 4

Example 1 was followed but the stock vessel was charged with 260 kg of cyclohexane and 178.3 kg of triisobutylaluminum. 7.7 kg of water (ratio water/TIBA=0.48) were metered into this circulating material via the JLR. 442 kg of a 30.2% strength triisobutyl aluminoxane (TIBAO) solution were formed. The yield based on the Al content was 100%. The cryoscopic determination of the average molecular weight gave 400 g/mol.

Example 5

Example 1 was followed but the stock vessel was charged with 240 kg of hexane and 82.8 kg of triisobutylaluminum. 5.66 kg of water (molar ratio water/TIBA=0.75) were metered into this circulating material via the JLR. 293 kg of a 17.1% strength hexaisobutyltetraaluminoxane solution (HIBAO, average molecular weight: 1100 g/mol, yield based on aluminum: 100% of theoretical) were produced.

Example 6

Example 1 was followed but 216.3 kg of heptane and 70.5 kg of triisobutylaluminum were reacted with 6.22 kg of water (molar ratio water/TIBA=0.97). 239.5 kg of 15.0% strength isobutylaluminoxane solution were obtained (IBAO, average molecular weight: 1800 g/mol, yield based on aluminum: 98% of theoretical).

What is claimed is:

1. A process for the preparation of aluminoxanes of the general formula $R_2AlO[RAlO]_nAlR_2$ or $[-(R)AlO-]_{n+3}$ wherein:

R is a branched or linear $C_1-C_{10}$-alkyl group, each of the radicals R is identical or different and each n is an integer from 0–20, by addition of water to a solution of trialkylaluminum of the formula $Al(R)_3$ in an aliphatic, cycloaliphatic or aromatic hydrocarbon solvent therefor whereby said water undergoes reaction with said trialkylaluminum to form said aluminoxane, characterized in that the water required for the reaction is metered via a mixing nozzle into said solution in a static mixer.

2. A process according to claim 1, characterized in that the static mixer used is a jet loop reactor.

3. A process according to claim 1, characterized in that the water is metered into the reactor in a volume flow ratio of water to said solution of trialkylaluminum of from 1:500 to 1:40,000.

4. A process according to claim 1, characterized in that the reaction is carried out at from −20° C. to +100° C.

5. A process according to claim 1, characterized in that each R is a methyl group.

6. A process according to claim 1 characterized in that the water added to said solution conforms to a molar ratio of $H_2O$:trialkylaluminum compound in the range of 0.6–1.2:1.

7. A process according to claim 1, characterized in that the water added to said solution conforms to a molar ratio of $H_2O$:trialkylaluminum compound in the range from 0.65:1 to 0.75:1, and the trialkylaluminum compound is trimethylaluminum.

8. A process according to claim 7, characterized in that the water is metered into the reactor in a volume flow ratio of water to said solution of trialkylaluminum of from 1:2,000 to 1:20,000.

* * * * *